United States Patent [19]

Weltman

[11] Patent Number: 4,689,311

[45] Date of Patent: Aug. 25, 1987

[54] SCREENING ANTIBODIES FOR CAPACITY TO DELIVER TOXIN TO TARGET CELLS

[75] Inventor: Joel K. Weltman, Barrington, R.I.

[73] Assignee: Rhode Island Hospital, Providence, R.I.

[21] Appl. No.: 782,206

[22] Filed: Sep. 30, 1985

[51] Int. Cl.$^4$ .................. G01N 33/53; A61K 31/00
[52] U.S. Cl. .............................. 436/519; 424/85; 435/7; 435/29; 436/547; 436/548; 530/389
[58] Field of Search .................. 436/547, 519, 548; 424/85; 530/389; 535/7, 29

[56] References Cited

U.S. PATENT DOCUMENTS

| | | | |
|---|---|---|---|
| 4,340,535 | 7/1982 | Voisin | 424/85 X |
| 4,401,764 | 8/1983 | Smith | 436/547 X |
| 4,468,382 | 8/1984 | Bacha | |
| 4,543,211 | 9/1985 | Kato | 514/12 X |

FOREIGN PATENT DOCUMENTS 2550944  3/1985  France .

OTHER PUBLICATIONS

Chemical Abstracts, 103:109913w (1985).
Murphy, J. R. et al., J. Clin. Microbiol., 7(1), 91–96 (1978).

Primary Examiner—Sidney Marantz

[57] ABSTRACT

Treatment and screening materials and methods (as for cancer) are provided in which there is provided between a toxin and an anticancer antibody an intermediate antibody with an affinity for either the toxin or the anticancer antibody.

6 Claims, No Drawings

SCREENING ANTIBODIES FOR CAPACITY TO DELIVER TOXIN TO TARGET CELLS

BACKGROUND OF THE INVENTION

This invention relates to the use of antibodies to deliver toxins to particular classes of unwanted cells, e.g., cancer cells.

The use of antibodies to target and deliver toxins to cancer cells has been reported in a number of patents and publications. For example, Voisin et al. U.S. Pat. No. 4,340,535, hereby incorporated by reference, describes such an antibody/toxin complex (an "immunotoxin") composed of an antibody covalently bonded via a disulfide linkage to the toxic A chain of ricin.

SUMMARY OF THE INVENTION

In general, the invention features a composition composed of a toxin linked to an antigen non-specific, species specific antibody. (As used herein, the term "antigen non-specific" refers to antibodies which, although specific in the sense that they preferentially bind to cells of a particular mammalian species (i.e., species specific), e.g., rabbits or mice, do not preferentially bind to a particular class of cells, e.g., cancer cells (i.e., are antigen non-specific).

The toxin can be covalently bonded to the non-specific antibody or, more preferably, the two can be linked via an anti-toxin antibody which is covalently bonded to the antigen non-specific antibody.

In another preferred embodiment, the antigen non-specific, species specific antibody of the composition is complexed with an antibody which is derived from (i.e., produced in) the mammalian species for which the antigen non-specific antibody is species-specific, and which is antigen-specific for a class of unwanted cells; compositions of this embodiment can be used as immunotoxins in which the antigen-specific "targeting" antibody is linked to the toxin via the antigen non-specific antibody, rather than by a cross-linking reagent, so that chemical modifications which potentially could interfere with binding or specificity are avoided.

The invention also features a method of measuring the capacity of an antibody produced in a mammal to deliver a toxin to a class of unwanted cells, involving contacting the antibody with cells of the unwanted class and with certain of the compositions set forth in the first two paragraphs of the Summary (namely those not complexed as set forth in the paragraph just above, and in which the species for which the species-specific antibody is specific is the same as that of the mammal in which the antigen-specific antibody was produced), and then measuring cell death as a measure of the capacity of the antibody to deliver the toxin to the class of unwanted cells. This method can be employed to screen a mixture of antibodies for those possessing comparatively greater capacity than others to deliver the toxin to the cells. The new method, employing these compositions (which are in effect universal screening reagents), can provide simple, fast screening of antibodies for potential cytotoxic capacity without requiring that each antibody be made into a cytotoxin prior to screening.

This invention relates to new materials and methods useful in cancer research and treatment.

It is known to make an "immunotoxin" by joining a toxin (cancer cell killer) to an anticancer antibody (cancer cell hunter, typically made by injecting the cancer cells into mice and then culturing the hybridomas formed from the latter) by a chemical, covalent bond. This has the disadvantage of tending to degrade both the toxin and the anticancer antibody.

I have discovered that an improved material results if the toxin is joined not to the anticancer antibody, but rather to an intermediate antibody having "affinity" (immunoaffinity) for either the toxin or the anticancer antibody. In particularly preferred embodiments, a second intermediate antibody is included, this having affinity for the other of the toxin and the anticancer antibody; and the two intermediate antibodies are joined by chemical covalency.

Particularly useful screening compounds and methods are provided by using an outer (not linked with the toxin except by a chemical bond or through a second intermediate antibody) intermediate antibody with an affinity for an anticancer antibody of a set the performance of which is to be comparison tested.

The broad invention permits securing against chemical degradation of either toxin or anticancer antibody; and in preferred embodiments permits securing against such degradation of both.

Other features and advantages of the invention will be apparent from the following description of the preferred embodiments thereof, and from the claims.

DESCRIPTION OF THE PREFERRED EMBODIMENTS

Preferred compositions and methods of the invention will now be described.

Universal Screening Reagent

A universal screening reagent precursor consisting of anti-ricin antibody covalently linked to non-specific anti-rabbit antibody was made as follows.

Immunospecifically purified goat anti-ricin ($6\times10^{-6}$M) (obtained from Vector Labs) and anti-rabbit IgG ($6\times10^{-6}$M) (which had been affinity-purified on rabbit IgG-diaminohexane agarose and obtained from U.S. Biochemical Corporation) were reacted together with 0.02M glutaraldehyde and 0.013M 3, 3'-iminobispropylamine in 0.15M NaCl-0.05M $Na_2PO_4$, pH 7.6, at room temperature for one hour. $NaBH_4$ (0.02M) was then added, and the cross-linking reaction quenched with 0.02M ethanolamine pH 7.6. The cross-linked antibody composition was dialyzed and then sterilized prior to use by filtration through a 0.22 micron-filter (Millex GV). The addition of ricin to the precursor completes the synthesis of the universal screening reagent in which ricin and anti-rabbit antibody are linked via the anti-ricin antibody.

Cell-Specific Conjugate

A cell-specific conjugate consisting of anti-ricin antibody covalently linked to anti-small cell carcinoma antibody was made as follows.

The first step, production of anti-small cell carcinoma antibodies, was carried out using cells of the H69 cell line, which were maintained in RPMI-1640 medium supplemented with 10% FCS in an atmosphere containing 10% carbon dioxide. Balb/c mice and randomly bred rabbit were repeatedly immunized, using conventional techniques, with H69 cells in complete Freund's adjuvant. The Ig fraction of the serum was obtained by precipitation with ammonium sulfate at one-third saturation.

The mouse anti-small cell carcinoma polyclonal antibody was cross-linked to goat anti-ricin using glutaraldehyde, as described above.

Screening Use of Universal Screening Reagent

The universal screening reagent described above was used to screen a heterogeneous population of rabbit anti-small cell carcinoma antibodies (prepared as described above), as follows.

Each anti-small cell carcinoma antibody sample (20 micrograms) was incrbated with approximately 188,000 H69 cells in a one ml volume. The control was normal rabbit immunoglobulin. The universal screening reagent precursor (anti-ricin crosslinked to anti-rabbit antibody) described above was then added 201 mcg in conjunction with Ricin A chain (E-Y Laboratories), at a concentration of $1 \times 10^{-8}$M in 1 ml RPMI-1640 containing 0.1M lactose.

Incubation of the cells with the universal screening reagent was one hour in duration, and was followed by two washes with 2 ml ice cold Dulbecco's phosphate buffered saline. Protein synthesis, an inverse measure of cell death, was determined by incubating 15,625 of the above-treated H69 cells with 0.25McC $^{14}$C leucine in 0.1 ml leucine-free RPMI-1640 containing 0.1M lactose at 37° C., and measuring $^{14}$C-leu uptake as counts per minute (CPM). As a control, CPM for cells incubated with medium in the absence of the universal screening reagent was determined. Killing of H69 tumor cells by indirect immunotoxin is shown (anti-tumor activity of indirect immunotoxin; numbers are means and standard deviations of triplicate determinations):

| IMMUNOGLOBULIN | C14 LEUCINE COUNTS PER MINUTE |
|---|---|
| Normal Rabbit | 194 ± 24 |
| Rabbit anti-H69 | 33 ± 17 |

Decreased $^{14}$C-leu uptake compared to the control indicated cell death caused by delivery of the ricin A chain to the H69 cells. The lower the $^{14}$C-leu uptake, the more effective was the antismall cell carcinoma cell antibody in delivering the ricin A to the H69 cells.

The mechanism for toxin delivery is believed to be as follows. In the presence of the cells, the reagent precursor (anti-ricin/anti-rabbit immunoglobulin conjugate) is linked to ricin A chain by immunoaffinity; the anti-small cell carcinoma antbody also binds to the reagent precursor by immunoaffinity and then delivers the ricin-containing complex to the H69 cells. The more efficient the delivery of the toxin to the cells by the anti-small cell carcinoma antibody, the more pervasive is cell death, and the lower is $^{14}$C-leu uptake.

Therapeutic Use of Universal Screeninq Reagent

To prepare an immunotoxin for therapeutic use, the reagent precursor, above, is mixed with ricin A chain and rabbit antibody against any unwanted class of cells, e.g., cancer cells such as small cell carcinoma cells; both the antibody and the ricin A chain bind to the reagent precursor by immunoaffinity. The immunotoxin is then administered to a patient in the same manner that other ricin-based immunotoxins have been administered; e.g., as described in Voisin et al., id.

Use of Cell-Specific Conjuqate

The cell-specific conjugate, above, can be used to treat small cell carcinoma, in the same manner that other ricin-based immunotoxins have been used; e.g., as described in Voisin et al., id.

The conjugate described above was tested for its ability to kill H69 cells as follows. The conjugate and ricin A chain (in solution, as described above) were, incubated with H69 ceils, the cells washed, and 100,000 of the cells were then incubated with 0.25 McC $^3$H-Leucine; CPM was measured as above as a measure of protein synthesis and an inverse measure of cell death.

Other Embodiments

Other embodiments are within the following claims.

For example, any toxin can be used which can be linked to an antibody; another example is diphtheria toxin, a portion of which has been linked to melanocyte stimulating hormone to produce a targeted cytotoxin (Bacha et al. U.S. Pat. No. 4,468,382, hereby incorporated by reference). The various antibodies can be derived from any suitable mammalian species, and the antibodies to the class of unwanted cells can be monoclonal or polyclonal. The determination of cell death can be carried out using any of a variety of isotopic and non-isotopic techniques, e.g., pH-dependent coloromet-ric methods such as the method described in J. Clin. Microbiol. 7, 91.

I claim:

1. A method of determining which first antibodies in a group of first antibodies possess the capacity effectively to deliver a toxin to a predetermined class of target cells, in a manner to inactivate said cells, said method comprising
   individually adding to said target cells separate first antibodies of said group and a universal screening agent comprising a toxin linked to a second antibody which recognizes all said first antibodies,
   separately measuring inactivation of cells to which said first antibodies and said universal screening agent had been added,
   comparing inactivation of target cells associated with the separate first antibodies, and
   determining which of the group of first antibodies has the desired capacity.

2. The method of claim 1 wherein said toxin is covalently linked to said second antibody.

3. The method of claim 1 wherein said second antibody is covalently linked to a third antibody that is antitoxin.

4. The method of claim 1 wherein said first antibodies are polyclonal.

5. The method of claim 1 wherein said group of first antibodies is obtained from a heterogeneous population of anticancer antibodies.

6. The method of claim 1 wherein said group of first antibodies comprises a group of monoclonal antibodies.

* * * * *